United States Patent [19]
Heath et al.

[11] Patent Number: 5,653,590
[45] Date of Patent: Aug. 5, 1997

[54] KIT OF ENDODONTIC INSTRUMENTS AND METHOD OF UTILIZING SAME

[75] Inventors: Derek E. Heath; Jerry A. Mooneyhan, both of Johnson City, Tenn.

[73] Assignee: Tulsa Dental Products, L.L.C., Tulsa, Okla.

[21] Appl. No.: 470,363

[22] Filed: Jun. 6, 1995

[51] Int. Cl.⁶ ................................................ A61C 5/02
[52] U.S. Cl. ........................................ 433/102; 433/224
[58] Field of Search ............................... 433/102, 224

[56] References Cited

U.S. PATENT DOCUMENTS

| | | | |
|---|---|---|---|
| 4,332,561 | 6/1982 | McSpadden | 433/102 |
| 4,836,780 | 6/1989 | Buchanan . | |
| 4,871,312 | 10/1989 | Heath | 433/164 |
| 4,934,934 | 6/1990 | Arpaio, Jr. et al. | 433/102 |
| 4,971,556 | 11/1990 | Ritano | 433/102 |
| 5,017,138 | 5/1991 | Schilder | 433/102 |
| 5,026,284 | 6/1991 | Martin | 433/102 |
| 5,106,298 | 4/1992 | Heath et al. | 433/102 |
| 5,125,838 | 6/1992 | Seigneurin | 433/102 |
| 5,219,284 | 6/1993 | Velvart et al. | 433/102 |
| 5,257,934 | 11/1993 | Cossellu | 433/102 |
| 5,380,200 | 1/1995 | Heath et al. | 433/102 |
| 5,464,362 | 11/1995 | Heath et al. | 433/102 X |
| 5,503,554 | 4/1996 | Schoeffel | 433/102 |

OTHER PUBLICATIONS

*Journal of Endodontics; An Initial Investigation of the Bending and Torsional Properties of Nitinol Root Canal Files;* vol. 14, No. 7, Jul. 1988, pp. 346–351.

Primary Examiner—Nicholas D. Lucchesi
Attorney, Agent, or Firm—Bell, Seltzer, Park & Gibson, P.A.

[57] ABSTRACT

A kit of endodontic instruments which are adapted for use in performing root canal therapy, and wherein the instruments in the kit have increasing diameters and differing tapers. The instruments are designed to be used sequentially in root canal therapy, and the difference of the tapers serves to prevent the whole working length of the instruments from being engaged with the wall of the tapered canal being formed, to thereby reduce the frictional loading of the instruments and the risk of breakage.

15 Claims, 2 Drawing Sheets

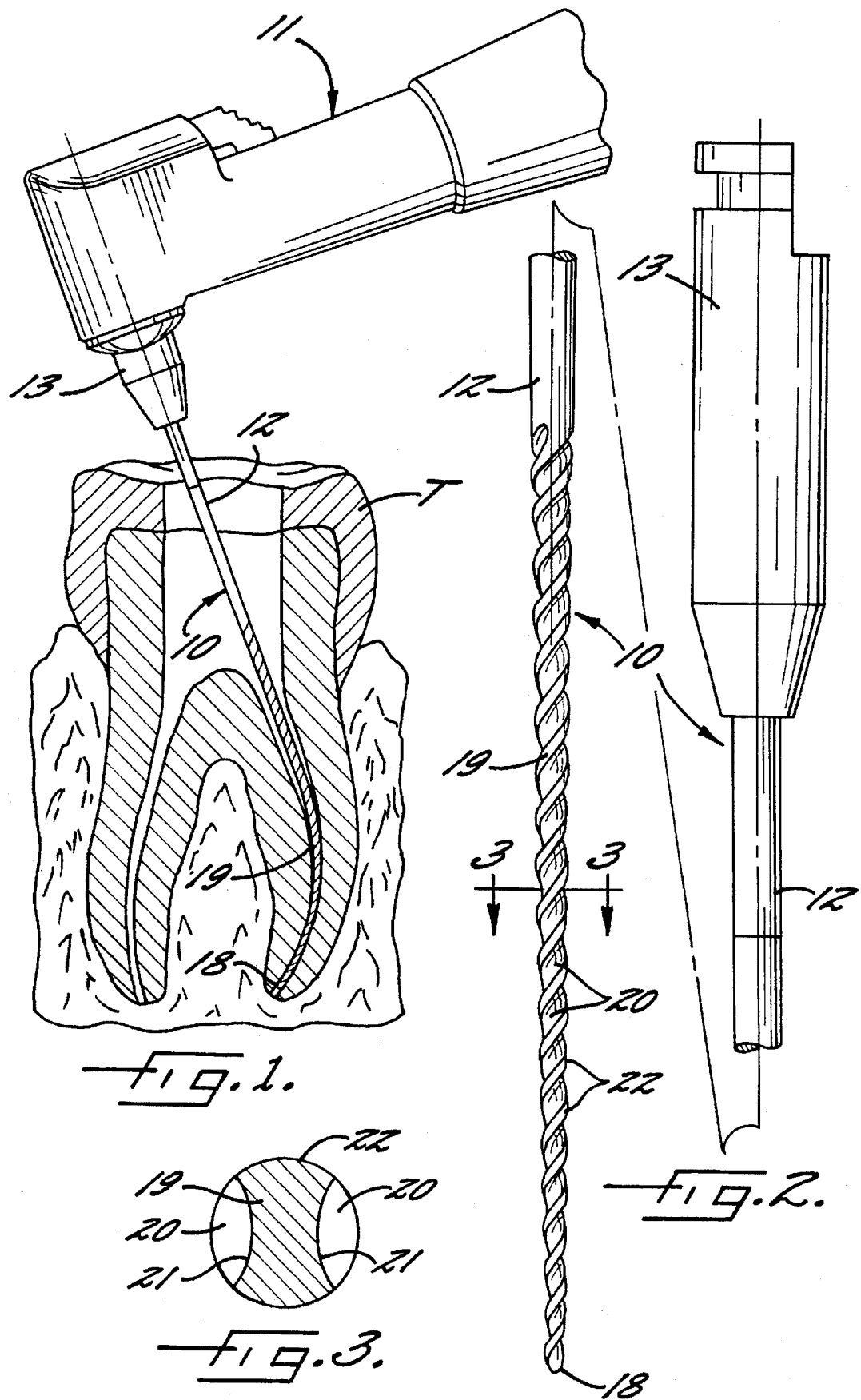

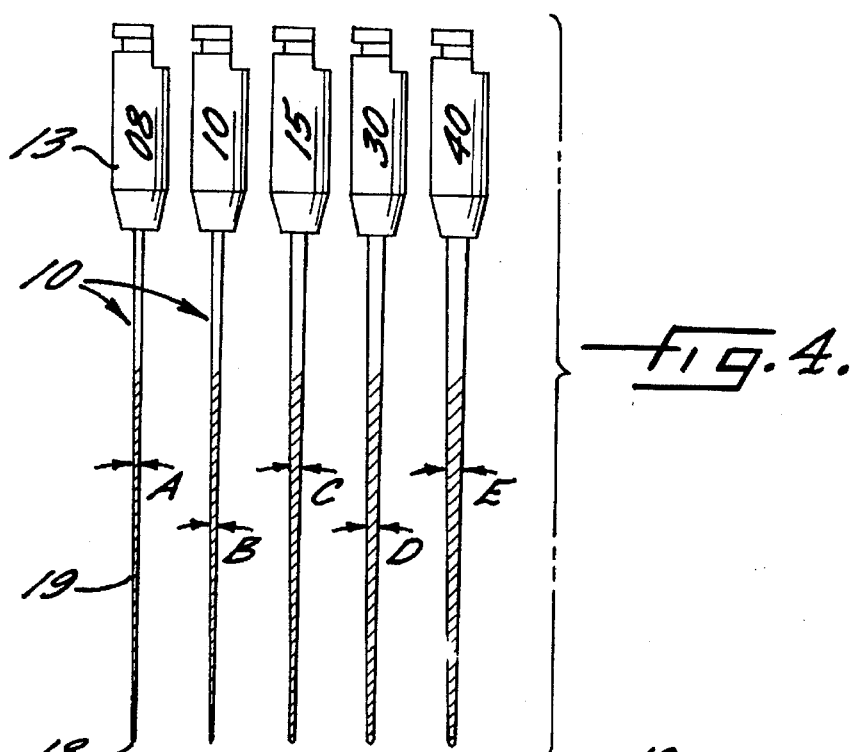
Fig. 4.
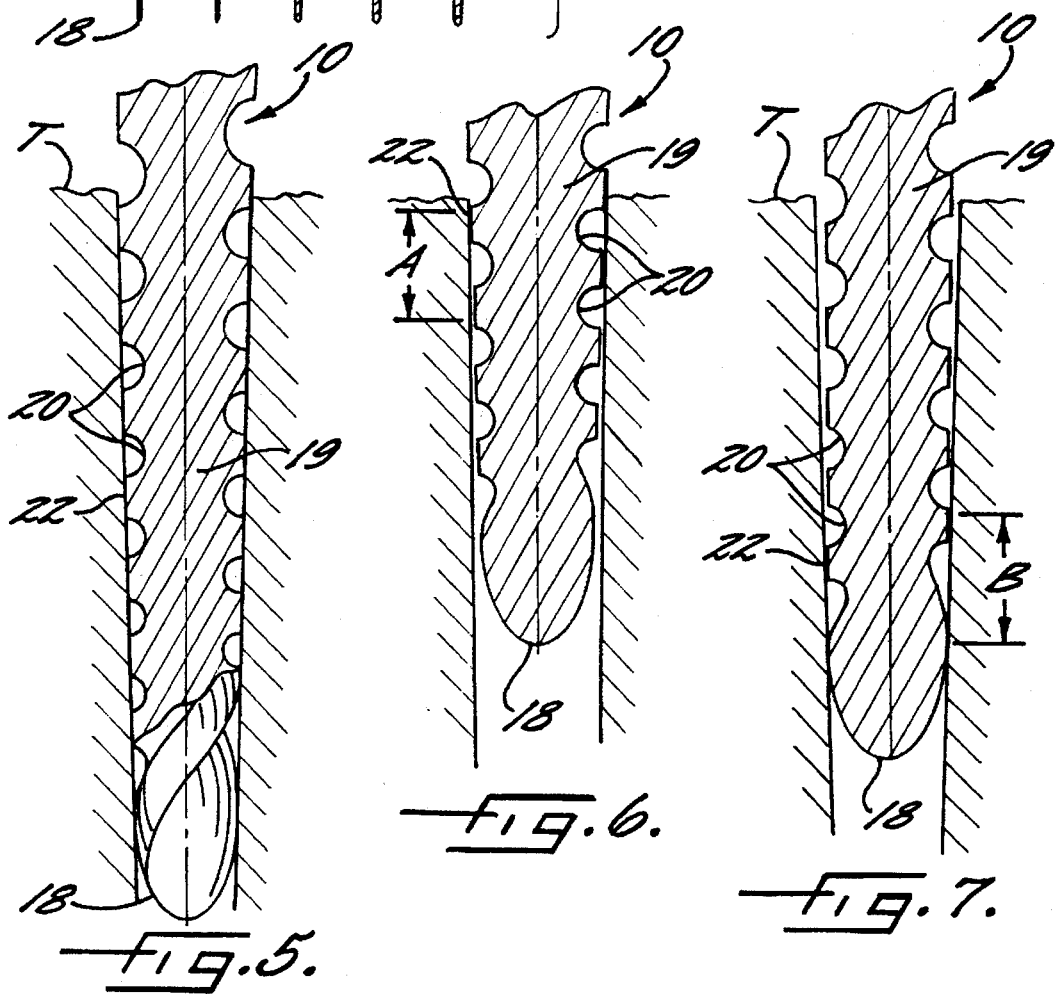
Fig. 5.
Fig. 6.
Fig. 7.

KIT OF ENDODONTIC INSTRUMENTS AND METHOD OF UTILIZING SAME

BACKGROUND OF THE INVENTION

The present invention relates to the field of endodontic instruments which are adapted for use in performing root canal therapy on teeth, and which are characterized by high flexibility and high resistance to torsional breakage.

Root canal therapy is a well-known procedure wherein the crown of a diseased tooth is opened so as to permit the canal to be cleaned and then filled. More particularly, after opening the crown, a series of very delicate, flexible instruments which are commonly called files are used to clean out and shape the root canal. Each file is rotated either manually or by a powered dental handpiece and reciprocated in the canal by the clinician, and files of increasingly larger diameter are used in sequence, to achieve the desired cleaning and shaping. When the canal is thus prepared, it is solidly filled with a filling material, which typically comprises a waxy, rubbery compound known as gutta percha. In one procedure, the gutta percha is positioned on an instrument called a compactor, and the coated compactor is inserted into the prepared canal and rotated and reciprocated to compact the gutta percha therein. The clinician then fills the tooth above the gutta percha with a protective cement, and lastly, fits a crown to the tooth.

Endodontic files of the described type are commonly supplied to the clinician in kits which comprise several files of increasing diameter. In particular, and in accordance with ANSI/ADA Specification No. 28-1988, files are provided in diameters which range from 0.08 mm at the tip (size 08) to 1.40 mm at the tip (size 140), and the files are provided in kits which contain a number of files of increasing diameter so that the files from a particular kit may be used in sequence by the clinician in accordance with the requirements of the particular canal being cleaned. Also, in the conventional kits, the working length of each file in the kit is tapered, at an included angle of between about ½ and 4 degrees, and with the tapers of all of the files in the kit being the same.

As is well-known by clinicians, procedural errors and accidents occasionally occur during root canal therapy, one of the most serious being the breakage of a file in the canal, since the remaining file fragment often cannot be removed from the canal. Such breakage can result from the rapid flexing of the file while it is being rotated in a curved canal. In addition, since the tapered configuration of the canal which is being formed will necessarily match the taper of the file, a locking interconnection can be formed between the wall of the canal and the surface of the rotating file along the full length of the file, and this locking interconnection results in a frictional binding which can severely stress the file and result in its breakage. This problem is particularly pronounced when the file is rapidly rotated in the canal by a powered dental handpiece, although the problem is also believed to be present when the file is rotated by hand.

Recently, endodontic files composed of a nickel-titanium alloy have been introduced, which provide a high degree of flexibility in both bending and torsion, and superior resistance to breakage, as compared to stainless steel instruments. In this regard, reference is made to the article entitled "An Initial Investigation of the Bending and the Torsional Properties of Nitinol Root Canal Files", *Journal of Endodontics*, Volume 14, No. 7, July 1988, at pages 346–351, and to copending U.S. application Ser. No. 08/271, 645, now U.S. Pat. No. 5,464,362.

While the use of nickel-titanium instruments is seen to significantly reduce the breakage problem, it is an object of the present invention to provide a kit of tapered endodontic instruments which are configured to avoid a locking interconnection between the wall of the tapered canal being formed and the tapered instrument, when the instrument is rapidly rotated in the canal by a machine driven handpiece, to thereby avoid excessive stress being placed on the instrument and so as to further minimize the risk of breakage of the instrument in the canal.

SUMMARY OF THE INVENTION

The above and other objects and advantages of the present invention are achieved in the embodiment illustrated herein by the provision of a kit of endodontic instruments which are adapted for use in performing root canal therapy, with each of the instruments comprising an elongate shank having a proximate end and an opposite pilot end and so as to define a working length adjacent the pilot end. The working length of each of the instruments has at least one continuous helical cutting edge formed along the length thereof, and with the shanks of the instruments in the kit having progressively increasing diameters at their pilot ends.

The working length of the shank of each of the instruments in the kit is also tapered toward the associated pilot end, with at least one of the instruments in the kit having a taper which differs from the taper of at least one of the remaining instruments in the kit.

In the preferred embodiment, the instrument in the kit having the smallest diameter has a predetermined taper, and the remaining instruments each have a taper which differs from that of the next progressively smaller diameter instrument. Thus when the instruments of the kit are used in sequence by the dentist, the second and subsequent instruments used in the procedure will not match the taper of the canal formed by the previously used instrument, but will contact the wall of the tapered canal along only a portion of the length of the instrument rather than along the full length thereof. Thus the locking forces which inherently develop when a tapered instrument is inserted into a correspondingly tapered canal, do not occur.

Also in the preferred embodiment, the cutting edge of each of the instruments in the kit is defined by a helical flute which defines a curved concave wall when viewed in transverse cross section, and so that a cutting edge is formed along each side edge of the curved concave wall. Also, a helical peripheral land is positioned between axially adjacent flute segments. Further, in the preferred embodiment, the shank of each of the instruments in the kit comprises a nickel-titanium alloy which provides a high degree of flexibility and is resistant to breakage.

The endodontic procedure of the present invention includes the steps of inserting a selected one of the instruments in the above described kit in the root canal and rotating and reciprocating the instrument so as to extirpate the canal and form the canal into a general conical configuration including a relatively wide crown portion and an apex at the inner end of the root canal, and withdrawing the selected first one of the instruments from the canal and inserting a selected second one of the instruments in the canal, with the selected second one of the instruments having a larger diameter and a taper which differs from that of the selected first one of the instruments, and rotating and reciprocating the selected second one of the instruments so as to extirpate the canal and further form the canal into a general conical configuration. Subsequently, the selected second one of the instruments is withdrawn from the canal and a selected third one of the instruments is inserted in the canal, with the selected third one of the instruments having a larger diameter and a taper which differs from that of the selected second one of the instruments, and rotating and reciprocating the selected third one of the instruments so as to extirpate the canal and further form the canal into a general conical configuration.

BRIEF DESCRIPTION OF THE DRAWINGS

Some of the objects and advantages of the present invention having been stated, others will appear as the description proceeds, when taken in conjunction with the accompanying drawings, in which FIG. 1 is a sectional side elevation view of a tooth undergoing root canal therapy, utilizing a machine driven endodontic instrument or file in accordance with the present invention;

FIG. 2 is a side elevation view of the instrument shown in FIG. 1, shown removed from the rotary handpiece;

FIG. 3 is a transverse sectional view of the shank of the instrument;

FIG. 4 is a side elevational view of a kit of instruments in accordance with the present invention; and FIGS. 5–7 are schematic representations of the procedure for using the instruments of the kit shown in FIG. 4 in accordance with the present invention.

DETAILED DESCRIPTION OF THE DRAWINGS

Referring more particularly to the drawings, wherein like numerals reference like parts, an endodontic instrument or file which embodies the features of the present invention is indicated generally at 10. In FIG. 1 the instrument is illustrated as being mounted in a conventional powered dental handpiece 11 in an operative position in a typical root canal in a tooth T. The instrument 10 comprises a shank 12 which is composed of a metallic alloy as further described below, and which typically has a length of about 30 mm. The shank 12 also includes an outer or proximate end which mounts a conventional machine (i.e. powered dental handpiece) engageable handle 13. The portion of the shank immediately below the handle is cylindrical and has a diameter of between about 0.5 and 1.6 mm, and this shank portion may include calibrated depth markings (not shown) of conventional design. The shank further includes an opposite distal or pilot end 18, shown best in FIG. 2, and a working length 19 which is defined adjacent the pilot end 18. The working length is slightly tapered toward the pilot end 18 at an included angle of between about one-half and four degrees.

In the preferred embodiment, the shank 12 has a relatively high flexibility, and it is composed of nickel-titanium alloy which has a very low modulus of elasticity, only one-fourth to one-fifth the value for stainless steel, and a very wide range of elastic deformation. The alloy preferably comprises at least about 40% titanium and at least about 50% nickel, and most preferably "55-Nitinol" alloy is used which contains 54–56 weight percent nickel with the balance comprising titanium. This alloy possesses unique mechanical memory, is non-magnetic, is corrosion resistant and has a relatively low density of 0.234 lb. per cu. in.

The working length 19 of the instrument 10 further comprises two continuous helical flutes 20 which extend along its length. The flutes are preferably machined in the outer surface of the shank in the manner further described in U.S. Pat. No. 4,934,934 and U.S. Pat. No. 5,464,362. This machining operation preferably results in a cross section as seen in FIG. 3. More particularly, each of the two flutes 20 defines a curved concave wall 21 when viewed in transverse cross section, and a helical land 22 is positioned between axially adjacent flute sections. Alternatively, a machining operation may be employed which produces a triangular or quadrangular cross section (not shown).

As noted above, it is conventional to package a plurality of the instruments 10 as described above in kits, with the instruments in a kit having a progressively increasing size, i.e. diameter, but uniform taper. Such packaging facilitates their use by the clinician, since the instruments are adapted to be serially used in performing root canal therapy. The progressively increasing diameters may be indicated by the size designations printed on the handles 13, or the size may be indicated by the color of the handle, as is conventional.

As an important and novel feature of the present invention, at least one of the instruments 10 in the kit has a taper which differs from the taper of at least one of the remaining instruments in the kit. As a specific example, the instrument in the kit having the smallest diameter has a predetermined taper of, for example, 0.02 mm difference in diameter per milliliter of working length, which results in an included angle of about 1°, while the remaining instruments in the kit have a taper which differs from that of the next progressively smaller diameter instrument, typically by between about ½ and 2 degrees included, and most preferably by between about ½ and 1 degrees.

A specific example of a kit which embodies the present invention will be described with reference to FIG. 4, which illustrates a kit composed of five instruments 10 ranging in size from size 08 to size 40. The working lengths of the instruments are tapered so as to have included angles as follows:

| Instrument Size | Included Angle |
| --- | --- |
| 08 | A = 1° |
| 10 | B = 2° |
| 15 | C = 3° |
| 30 | D = 2° |
| 40 | E = 3° |

FIGS. 5–7 schematically illustrate a typical procedure utilizing the kit of instruments 10 of the present invention, it being understood that these illustrations are simplified in order to better illustrate the novel features of the invention. In particular, the usual curvature of the canal has not been shown.

In FIG. 5, the initial instrument, which is the size 10 instrument from the kit shown in FIG. 4 and which has a taper of about 2°, is shown in the root canal of a tooth which has been formed by the rotation of the instrument in the canal. As will be understood, the canal has a taper which generally matches the taper of the instrument, since the rotation of the instrument serves to shape the canal into a corresponding taper.

The second step of the procedure is illustrated in FIG. 6, wherein the size 15 instrument, which has both a larger diameter and a greater taper than that of the size 10 instrument, is operatively positioned and rotated in the canal. Significantly, it will be noted that the size 15 instrument initially engages the canal at a single location A along its length, which is adjacent the crown end of the canal, by reason of the increased taper of the size 15 instrument. Also, by reason of its larger diameter, the pilot end of the size 15 instrument will be well short of the apex of the canal. Upon rotation of the size 15 instrument, and its advance downwardly into the canal, the size 15 instrument first cuts at the location A, and the cutting action moves downwardly toward the apex. Thus only a portion of the length of the instrument is engaged in the cutting action at a given time, and the loading of the instrument is thereby reduced. This reduced loading in turn serves to minimize the risk of breakage.

The third step of the illustrated procedure is illustrated in FIG. 7, wherein the size 30 instrument is employed, which has a larger diameter than the size 15 instrument but a taper less than that of the size 15 instrument and corresponding to that of the size 10 instrument. In this case, it will be noted that the size 30 instrument engages the canal at a single location B near the apex of the canal and the cutting action will move upwardly on the instrument as the instrument is moved downwardly. Here again, only a portion of the length of the instrument will be stressed during the cutting operation.

As an alternative to the use of an instrument of reduced taper as shown in FIG. 7, it is also possible to again utilize an instrument having a taper greater than that of the size 15 instrument used in FIG. 6. In this instance, the canal would be shaped in the manner described above with reference to FIG. 6, with the instrument again experiencing a reduced cutting load.

The above steps may be continued with instruments of increasingly larger diameter, and with each instrument having a taper which differs from that of the previously used instrument, until the canal is properly shaped and extirpated.

In the drawings and specification, there has been set forth preferred embodiments of the invention, and although specific terms are employed, they are used in a generic and descriptive sense only and not for purposes of limitation.

That which is claimed is:

1. A kit comprising a plurality of endodontic instruments which are adapted for use in performing root canal therapy,
    each of said instruments comprising an elongate shank having a proximate end and an opposite pilot end and so as to define a working length adjacent said pilot end, with the working length of each of said instruments having at least one continuous helical cutting edge formed along the length thereof, and with the shanks of all of the instruments in the kit having progressively increasing diameters at their pilot ends,
    the working length of the shank of each of said instruments in the kit being tapered toward the associated pilot end, with at least one of the instruments in the kit having a taper which differs from the taper of at least one of the remaining instruments in the kit by between about ½ and about 2 degrees.

2. The kit of endodontic instruments as defined in claim 1 wherein the working length of the shank of each of the instruments in the kit is tapered at an included angle of between about ½ and about 4 degrees.

3. The kit of endodontic instruments as defined in claim 2 further comprising a handle mounted at said proximate end of said shank.

4. The kit of endodontic instruments as defined in claim 3 wherein said at least one cutting edge of each of said instruments in said kit is defined by a helical flute which defines a curved concave wall viewed in transverse cross section, a cutting edge along each side edge of the curved concave wall, and a helical peripheral land positioned between axially adjacent flute segments.

5. The kit of endodontic instruments as defined in claim 4 wherein the shank of each of said instruments in said kit comprises a nickel titanium alloy.

6. The kits of endodontic instruments as defined in claim 1 wherein at least one of the instruments has a taper which is greater than that of the next progressively smaller diameter instrument, and at least another one of the instruments has a taper which is less than that of the next progressively smaller diameter instrument.

7. A kit comprising a plurality of endodontic instruments which are adapted for use in performing root canal therapy,
    each of said instruments comprising an elongate shank having a proximate end and an opposite pilot end and so as to define a working length adjacent said pilot end, with the working length of each of said instruments having at least one continuous helical flute formed along the length thereof and so as to define a cutting edge along each side of the flute and a helical peripheral land between adjacent flute segments, and with the shanks of all of the instruments in the kit having progressively increasing diameters at their pilot ends,
    the working length of the shank of each of said instruments in the kit being tapered toward the associated pilot end, with the instrument in the kit having the smallest diameter having a predetermined taper, and with the remaining instruments in the kit having a taper which differs from that of the next progressively smaller diameter instrument by between about ½ and about 2 degrees.

8. The kit of endodontic instruments as defined in claim 7 wherein the working length of the shank of each of the instruments in the kit is tapered at an included angle of between about ½ and about 4 degrees.

9. The kit of endodontic instruments as defined in claim 7 wherein the shank of each of said instruments in said kit consists essentially of an alloy which comprises at least about 40 percent titanium and at least about 50 percent nickel.

10. The kit of endodontic instruments as defined in claim 9 wherein said continuous flute of each of said instruments defines a curved concave wall viewed in transverse cross section, with said cutting edges being disposed along each side edge of the curved concave wall.

11. The kit of endodontic instruments as defined in claim 10 further comprising a machine engageable handle mounted at said proximate end of said shank of each of said instruments in said kit.

12. The kit of endodontic instruments as defined in claim 7 wherein at least one of said remaining instruments has a taper which is greater than that of the next progressively smaller diameter instrument, and another one of said remaining instruments has a taper which is less than that of the next progressively smaller diameter instrument.

13. The kit of endodontic instruments as defined in claim 12 wherein at least some of the instruments of the kit, when arranged to have progressively increasing diameters at their pilot ends, have alternately greater and smaller tapers.

14. An endodontic procedure comprising the steps of
    providing a plurality of endodontic instruments, with each of said instruments comprising an elongate shank having a proximate end and an opposite pilot end and so as to define a working length adjacent said pilot end, with the working length of each of said instruments having at least one continuous helical cutting edge formed along the length thereof, and with the shanks of the instruments having progressively increasing diameters at their pilot ends, the working length of the shank of each of said instruments being tapered toward the associated pilot end, with at least one of the instruments having a taper which differs from the taper of at least one of the remaining instruments, inserting a selected first one of the instruments in a root canal and rotating and reciprocating the instrument so as to extirpate the canal and form the canal into a general conical configuration including a relatively wide crown portion and an apex at the inner end of the root canal, and withdrawing the selected first one of the instruments from the canal and inserting a selected second one of the instruments in the canal, with the selected second one of the instruments having a larger diameter and a taper which differs from that of the selected first one of the instruments, and rotating and reciprocating the selected second one of the instruments so as to extirpate the canal and further form the canal into a general conical configuration, and then withdrawing the selected second one of the instruments from the canal and inserting a selected third one of the instruments in the canal, with the selected third one of the instruments having a larger diameter and a taper which differs from that of the selected second one of the instruments, and rotating and reciprocating the selected third one of the instruments so as to extirpate the canal and further form the canal into a general conical configuration.

15. The endodontic procedure as defined in claim 14 wherein the direction of change of the tapers between the third and second instruments is opposite the direction of change of the tapers between the second and first instruments.

* * * * *